United States Patent
He et al.

(10) Patent No.: US 10,188,552 B2
(45) Date of Patent: *Jan. 29, 2019

(54) SURGICAL SYSTEM PROVIDING HANDS-FREE CONTROL OF A SURGICAL TOOL

(71) Applicant: The Johns Hopkins University, Baltimore, MD (US)

(72) Inventors: Xingchi He, Columbia, MD (US); Iulian Iordachita, Lutherville-Timonium, MD (US); Yuki Horise, Baltimore, MD (US); Russell H. Taylor, Severna Park, MD (US); Peter L. Gehlbach, Monkton, MD (US)

(73) Assignee: The Johns Hopkins University, Baltimore, MD (US)

( * ) Notice: Subject to any disclaimer, the term of this patent is extended or adjusted under 35 U.S.C. 154(b) by 124 days.

This patent is subject to a terminal disclaimer.

(21) Appl. No.: 15/237,347

(22) Filed: Aug. 15, 2016

(65) Prior Publication Data
US 2017/0042730 A1 Feb. 16, 2017

Related U.S. Application Data

(60) Provisional application No. 62/205,554, filed on Aug. 14, 2015.

(51) Int. Cl.
*B25J 13/00* (2006.01)
*A61F 9/007* (2006.01)
(Continued)

(52) U.S. Cl.
CPC .... *A61F 9/00736* (2013.01); *A61B 17/00234* (2013.01); *A61B 34/30* (2016.02);
(Continued)

(58) Field of Classification Search
CPC ... A61B 19/46; A61B 17/00234; A61B 34/10; A61B 34/30; A61B 90/06; A61B 34/35;
(Continued)

(56) References Cited

U.S. PATENT DOCUMENTS 7,742,801 B2 * 6/2010 Neubauer .............. G16H 50/50
600/411
8,623,026 B2 * 1/2014 Wong ................. A61B 17/1703
29/592
(Continued)

OTHER PUBLICATIONS

Bourla et al., "Feasibility Study of Intraocular Robotic Surgery with the da Vinci Surgical System," Retina, The Journal of Retinal and Vitreous Diseases, vol. 28, No. 1, pp. 154-158 (2008).
(Continued)

*Primary Examiner* — Dalena Tran
(74) *Attorney, Agent, or Firm* — Venable LLP; Henry J. Daley

(57) ABSTRACT

A surgical system provides hands-free control of at least one surgical tool includes a robot having a tool connector, a smart tool attached to the tool connector of the robot, and a feedback control system configured to communicate with the smart tool to provide feedback control of the robot. The smart tool includes a tool that has a tool shaft having a distal end and a proximal end, a strain sensor arranged at a first position along the tool shaft, at least one of a second strain sensor or a torque-force sensor arranged at a second position along the tool shaft, the second position being more towards the proximal end of the tool shaft than the first position, and a signal processor configured to communicate with the strain sensor and the at least one of the second strain sensor or the torque-force sensor to receive detection signals therefrom. The signal processor is configured to process the detection signals to determine a magnitude and position of a lateral component of a force applied to the tool shaft when the position of the applied force is between the first and second positions. The feedback system controls the robot to move in response to at least the magnitude and position of the lateral component of the force applied to the tool shaft when the position of the applied force is between the first and second
(Continued)

positions so as to cancel the force applied to the tool shaft to thereby provide hands-free control of the at least one surgical tool.

20 Claims, 10 Drawing Sheets

(51) Int. Cl.

| | | |
|---|---|---|
| *A61B 34/30* | (2016.01) | |
| *A61B 34/37* | (2016.01) | |
| *A61B 34/35* | (2016.01) | |
| *A61B 90/00* | (2016.01) | |
| *A61B 90/30* | (2016.01) | |
| *A61B 17/00* | (2006.01) | |
| *G09B 19/24* | (2006.01) | |

(52) U.S. Cl.
CPC .............. *A61B 34/35* (2016.02); *A61B 34/37* (2016.02); *A61B 90/06* (2016.02); *A61B 90/30* (2016.02); *G09B 19/24* (2013.01); *A61B 2090/065* (2016.02); *A61B 2090/066* (2016.02)

(58) Field of Classification Search
CPC ......... A61B 34/72; A61B 34/76; A61B 34/77; G01L 1/246; G01L 5/166; G09B 19/24; A61F 9/00736; B25J 13/006; B25J 19/04; B25J 3/04; B25J 9/1689
USPC ...... 700/245, 257, 258; 318/568.1; 607/115, 607/116, 55
See application file for complete search history.

(56) References Cited

U.S. PATENT DOCUMENTS

2014/0052150 A1* 2/2014 Taylor ................ A61B 19/2203
606/130
2015/0342695 A1 12/2015 He et al.
2015/0374449 A1* 12/2015 Chowaniec ............ A61B 90/06
606/1

OTHER PUBLICATIONS

Cao et al., "Automatic Instrucment Tracking Endo-Illuminator for Intra-Ocular Surgeries," Journal of Medical Devices, vol. 8, pp. 030932-1-030932.3 (2014).
Gupta et al., "Surgical Forces and Tactile Perception During Retinal Microsurgery," in International Conference on Medical Image Computing and Computer-Assisted Intervention, LCNS 1679, pp. 1218-1225 (1999).
He et al., "A Multi-Function Force Sensing Instrument for Variable Admittance Robot Control in Retinal Microsurgery," in IEEE International Conference on Robotics and Automation, pp. 1411-1418 (2014).
Kummer et al., "OctoMag: An Electromagnetic System for 5-DOF Wireless Micromanipulation," IEEE Transactions on Robotics, vol. 26, No. 6, pp. 1006-1017 (2010).
Mitchell et al., "Development and Application of a New Steady-Hand Manipulator for Retinal Surgery," in IEEE International Conference on Robotics and Automation, pp. 623-629 (2007).
Song et al., "Fiber-optic OCT sensor guided "SMART" microforceps for microsurgery," Biomedical Optics Express, vol. 4, No. 7, pp. 1045-1050 (2013).
Sznitman et al., "Unified Detection and Tracking of Instruments During Retinal Microsurgery," IEEE Transactions on Pattern Analysis and Machine Intelligence, vol. 35, No. 5, pp. 1263-1273 (2013).
Taylor et al., "A Steady-Hand Robotic System for Microsurgical Augmentation," The International Journal of Robotics Research, vol. 18, No. 12, pp. 1201-1210 (1999).
Uneri et al., "New Steady-Hand Eye Robot with Micro-Rorce Sensing for Vitreoretinal Surgery," in IEEE International Conference on Biomedical Robotics and Biomechatronics, pp. 814-819 (2010).

* cited by examiner

SURGICAL SYSTEM PROVIDING HANDS-FREE CONTROL OF A SURGICAL TOOL

This application claims priority to U.S. Provisional Application No. 62/205,554 filed Aug. 14, 2015, the entire content of which is hereby incorporated by reference.

This invention was made with Government support of Grant No. R01 EB 000526 and BRP Grant 1 R01 EB 007969, awarded by the Department of Health and Human Services, The National Institutes of Health (NIH). The U.S. Government has certain rights in the invention.

BACKGROUND

1. Technical Field

The field of the currently claimed embodiments of this invention relates to surgical systems and tools, and more particularly to surgical systems providing hands-free control of at least one surgical tool and smart tools.

2. Discussion of Related Art

Retinal microsurgery refers to intraocular surgical treatment of disorders related to the retina, vitreous, and macula of the eye. Typical diseases include retina detachment, macular degeneration, and diabetic retinopathy. Retinal microsurgery demands advanced surgical skills that are near or beyond natural human capabilities. During retinal microsurgery, a surgical microscope is placed above the patient to provide magnified visualization of the interior of the eye. The surgeon inserts small instruments (e.g. 25 Ga) through trocars on the sclera, the white part of the eye, to perform delicate tissue manipulation in the posterior of the eye.

An example of a common surgical task is epiretinal membrane (ERM) peeling to restore the patient's vision from ERM distortion. The surgeon carefully peels the thin, semi-transparent scar tissue (the ERM) off the retina using a micro-forceps, as shown in FIGS. 1A and 1B. Steady and precise motion is desired, because the thickness of the ERM [1] can be an order of magnitude smaller than human hand tremor [2]. Additionally the force applied on the ERM has to stay below the strength of the retina tissue. However, the forces exerted between the instrument tip and the retina are well below the human sensory threshold [1]. The absence of force sensing raises the risk of applying excessive force on the retina, which can potentially cause retina hemorrhage and tearing. During the ERM peeling, the eye should be stable to minimize the motion of the target membrane. This requires the tool motion to comply at the sclerotomy site. Only three rotational degrees of freedom (DOF) about the sclera entry point and one translational DOF along the instrument axis are allowed, while lateral translations are prohibited by the sclera constraint. This corresponds to the concept of remote center-of-motion (RCM) in robotics, devised by Taylor et al. [4]. A fixed RCM is often considered to be a fundamental requirement in minimally invasive Surgery (MIS).

Unlike MIS, the imaging component of retinal microsurgery, the microscope, is located outside the patient and is rarely moved, as shown in FIG. 1A. Instead, the retinal surgeon needs to reposition the patient's eye while the tools are inserted, in order to adjust the view and gain tool access to the region of interest. As a result, the location of the RCM point (the sclera entry point) is not necessarily fixed, and can move up to 12 mm during retinal microsurgery [5]. The repositioning of the eye requires all of the instruments inserted in the eye (e.g. a micro-forceps and a light pipe) to move in coordination. Unsynchronized instrument motion can cause cornea striae, which distorts the view of the retina in the microscope. Suboptimal ergonomics and fatigue impose further limitations on surgical performance.

Many robotic systems have been developed and investigated to explore the potential to enhance and expand the capabilities of retinal surgery and microsurgery in general. Master-slave teleoperated robotic systems [6]-[10] have the advantage of motion scaling to achieve high precision. Building both master and slave robots results in complex systems and high cost. Furthermore, the surgeon's perception of the interaction between the slave robot and the patient is inadequate. Another approach is handheld robotic devices that provide active tremor cancellation [11][12]. Despite increased size and weight attributed to additional actuators, these devices provide an intuitive interface. However, the workspace is constrained by the tracking system and scaled feedback of the human-imperceptible forces cannot be implemented. The third approach is untethered micro-robots moved by controlled nonuniform magnetic fields [13]. The untethered control enables a large workspace and complex maneuvers. The drawbacks include the large footprint and limited surgical application.

Some embodiments of the current invention can use the Steady-Hand Eye Robot with hands-on cooperative control [14]-[17], where the user and the robot both hold the surgical instrument. The user input force applied on the instrument handle controls the velocity with which the robot follows the user motion. This control approach is also termed admittance velocity control. The human hand tremor is damped by the stiff robot structure. The cooperatively controlled robot provides not only the precision and sensitivity of a machine, but also the manipulative transparency and immediacy of hand-held instruments. This robotic system can further be augmented with virtual fixtures [18], as well as incorporated with smart instruments with various sensing modalities.

Virtual fixtures are algorithms that provide assistive motion guidance with anisotropic robot behavior. The robot motion constraints assist the user to avoid forbidden regions [18][19], as well as to guide along desired paths [20][21]. Virtual fixtures can be prescribed [18][19], generated from patient anatomy [22] or from real-time computer vision [20]. The implementation includes impedance [19] and admittance methods [20][21], as well as optimization algorithms with desired geometric constraints [22][23]. With the aid of virtual fixtures, the mental and physical demands on the user to accomplish a desired maneuver are reduced, while the task performance is notably increased. The surgeon can concentrate on the critical surgical tasks (e.g. ERM peeling) if virtual fixtures can manage the inherent surgical motion constraints, such as RCM and tool coordination, by providing an intuitive, guided robot behavior.

Smart instruments with force sensing capability are essential for safe interaction between the robot and the patient. Various force sensors have been developed for microsurgery, micromanipulation, and MIS [24]-[28] Handle mounted force sensors [29] cannot distinguish forces exerted at the tool tip from those at the trocar. Therefore, a family of force sensing instruments [30]-[33] has been developed with fiber optic sensors integrated into the distal portion of the instrument that is typically located inside the eye. Auditory [34] and haptic [35] force feedbacks have demonstrated the efficacy of regulating the tool-to-tissue interaction force. During a freehand manipulation, the surgeon can often sense the contact force at the sclera entry point, and utilizes it as an important indicator to guide the desired motion, e.g. RCM and tool coordination. However, the stiffness of the Steady-Hand Eye Robot attenuates the user perceptible level of the sclera force, inducing undesired large sclera forces. We devised a dual force sensing instrument [36] to provide force feedback from both tool tip force and sclera force. The drawback is that the force sensor cannot provide the sclera force value and the location where the sclera force is applied on the tool shaft. Instead, it measures the moment attributed to the sclera force. Therefore, there remains a need for surgical systems that provide hands-free control of at least one surgical tool and/or improved surgical tools and methods.

The following references are incorporated herein by reference.

P. K. Gupta, P. S. Jensen, and E. de Juan, "Surgical forces and tactile perception during retinal microsurgery," in *International Conference on Medical Image Computing and Computer-Assisted Intervention*, vol. 1679, 1999, pp. 1218-1225.

D. H. Bourla, J. P. Hubschman, M. Culjat, A. Tsirbas, A. Gupta, and S. D. Schwartz, "Feasibility study of intraocular robotic surgery with the da Vinci surgical system," *Retina Philadelphia Pa*, vol. 28, no. 1, pp. 154-158, January 2008.

C. Song, D. Y. Park, P. L. Gehlbach, S. J. Park, and J. U. Kang, "Fiber-optic OCT sensor guided "SMART" microforceps for microsurgery," *Biomedical Optics Express*, vol. 4, no. 7, pp. 1045-1050, 2013.

M. P. Kummer, J. J. Abbott, B. E. Kratochvil, R. Borer, A. Sengul, and B. J. Nelson, "OctoMag: An Electromagnetic System for 5-DOF Wireless Micromanipulation," *IEEE Transactions on Robotics*, vol. 26, no. 6, pp. 1006-1017, 2010.

R. Taylor, P. Jensen, L. Whitcomb, A. Barnes, R. Kumar, D. Stoianovici, P. Gupta, Z. Wang, E. Dejuan, and L. Kavoussi, "A Steady-Hand Robotic System for Microsurgical Augmentation," *The International Journal of Robotics Research*, vol. 18, no. 12, pp. 1201-1210, 1999.

B. Mitchell, J. Koo, I. Iordachita, P. Kazanzides, A. Kapoor, J. Handa, G. Hager, and R. Taylor, "Development and application of a new steady-hand manipulator for retinal surgery," in *IEEE International Conference on Robotics and Automation*, 2007, pp. 623-629.

Uneri, M. A. Balicki, J. Handa, P. Gehlbach, R. H. Taylor, and I. Iordachita, "New Steady-Hand Eye Robot with micro-force sensing for vitreoretinal surgery," in *IEEE International Conference on Biomedical Robotics and Biomechatronics*, 2010, pp. 814-819.

X. He, M. Balicki, P. Gehlbach, J. Handa, R. Taylor, and I. Iordachita, "A multi-function force sensing instrument for variable admittance robot control in retinal microsurgery," in *IEEE International Conference on Robotics and Automation*, 2014, pp. 1411-1418.

Thomas H. W, *Vitreoretinal Surgery*. Springer Berlin Heidelberg, 2013, ch. 2. K. Cao, R. Pinon, I. Schachar, T. Jayasundera, and S. Awtar, "Automated Instrument Tracking Endo-Illuminator for Intra-Ocular Surgeries," *Journal of medical Devices*, vol. 8, no. 3, 030932, 2014.

R. Sznitman, R. Richa, R. H. Taylor, B. Jedynak, and G. D. Hager, "Unified Detection and Tracking of Instruments During Retinal Microsurgery," *IEEE Transactions on Pattern Analysis and Machine Intelligence*, vol. 35, no. 5, pp. 1263-1273, 2013.

X. He, I. Iordachita, M. Balicki, and R. Taylor, "Multi-Function Force-Sensing Surgical Instrument and Method of Use for Robotic Surgical System," JHU Disclosure 12726, U.S. patent application Ser. No. 14/292,361, filed on May 30, 2014

SUMMARY

A surgical system that provides hands-free control of at least one surgical tool according to some embodiments of the current invention includes a robot having a tool connector, a smart tool attached to the tool connector of the robot, and a feedback control system configured to communicate with the smart tool to provide feedback control of the robot. The smart tool includes a tool that has a tool shaft having a distal end and a proximal end, a strain sensor arranged at a first position along the tool shaft, at least one of a second strain sensor or a torque-force sensor arranged at a second position along the tool shaft, the second position being more towards the proximal end of the tool shaft than the first position, and a signal processor configured to communicate with the strain sensor and the at least one of the second strain sensor or the torque-force sensor to receive detection signals therefrom. The signal processor is configured to process the detection signals to determine a magnitude and position of a lateral component of a force applied to the tool shaft when the position of the applied force is between the first and second positions. The lateral component of the force is a component of the force that lies in a plane that is orthogonal to the tool shaft at the position at which the force is applied. The feedback system controls the robot to move in response to at least the magnitude and position of the lateral component of the force applied to the tool shaft when the position of the applied force is between the first and second positions so as to cancel the force applied to the tool shaft to thereby provide hands-free control of the at least one surgical tool.

A method of at least one of providing feedback during a surgical procedure or during a surgical training session according to some embodiments of the current invention includes providing a smart tool, using the smart tool during the surgical procedure or the surgical training session, receiving signals from the smart tool regarding at least the magnitude and position of the lateral component of the force applied to the tool shaft during the surgical procedure or the surgical training session, and providing at least one of contemporary feedback during the surgical procedure or the surgical training session based on the received signals. The smart tool includes a tool that has a tool shaft having a distal end and a proximal end, a strain sensor arranged at a first position along the tool shaft, at least one of a second strain sensor or a torque-force sensor arranged at a second position along the tool shaft, the second position being more towards the proximal end of the tool shaft than the first position, and a signal processor configured to communicate with the strain sensor and the at least one of the second strain sensor or the torque-force sensor to receive detection signals therefrom. The signal processor is configured to process the signals to determine a magnitude and position of a lateral component of a force applied to the tool shaft when the position of the applied force is between the first and second positions. The lateral component of the force is a component of the force that lies in a plane that is orthogonal to the tool shaft at the position at which the force is applied.

A smart surgical tool according to some embodiments of the current invention includes a tool handle configured to be hand-held and to be attachable to and detachable from a robotic system, the tool handle having a proximal end and a distal end, a tool shaft attached to a distal end of the tool handle, the tool shaft having a distal end and a proximal end, a strain sensor arranged at a first position along the tool shaft, and at least one of a second strain sensor or a torque-force sensor arranged at a second position along the tool shaft, the second position being more towards the proximal end of the tool shaft than the first position. The tool handle has a quick-release portion to allow a user to remove the smart surgical tool from the robotic system to avoid or minimize damage during surgery if the robot malfunctions.

BRIEF DESCRIPTION OF THE DRAWINGS

Further objectives and advantages will become apparent from a consideration of the description, drawings, and examples.

DETAILED DESCRIPTION

Figure 1B:
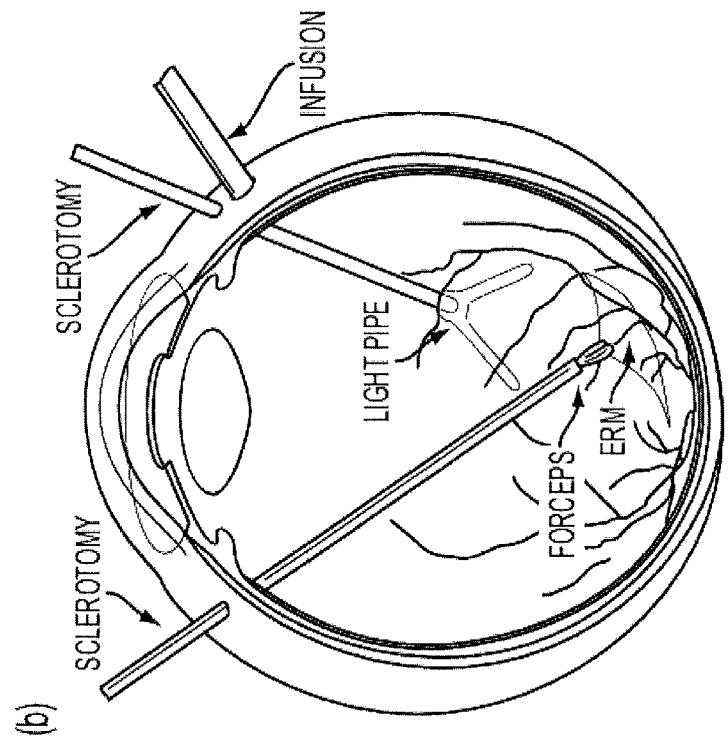
FIG. 1B is a schematic illustration of an undergoing a surgical procedure.
Figure 1A:
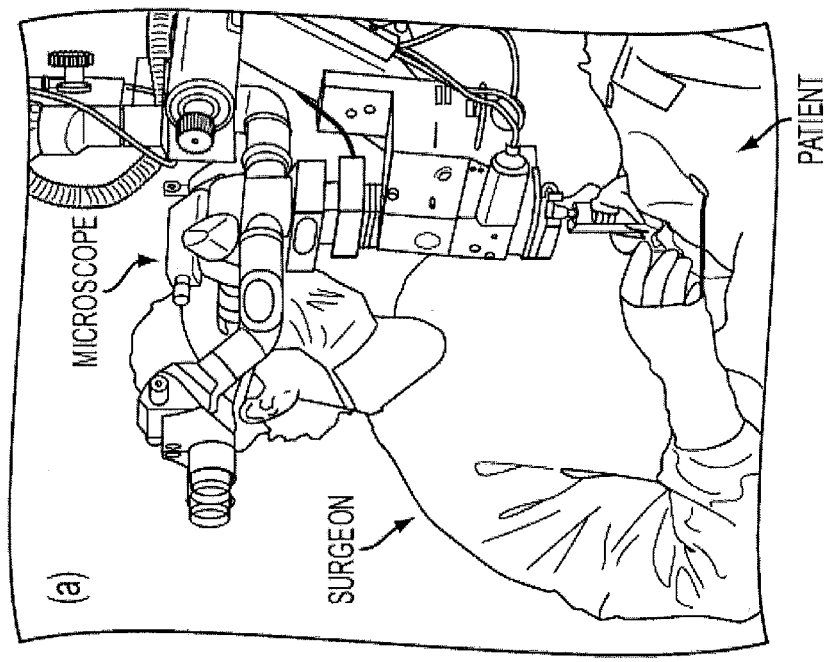
FIG. 1A shows an example of a surgical setup in which the surgeon uses a specialized microscope to perform microsurgery on a patient's eye.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The U.S. patent application Ser. No. 14/292,361, filed May 30, 2014, which is assigned to the same assignee as the current application, is hereby incorporated by reference herein in its entirety for all purposes.

An embodiment of the current invention is directed to a sensorized ophthalmic endo-illuminator that can sense forces applied along the tool shaft, including the location where the forces are applied on the tool shaft. When this endo-illuminator is in freehand use, its sensor measurements can be used to assess and assist surgical training as well as provide a quantitative record of surgical procedures. This sensorized endo-illuminator can also be incorporated into a robot as a robotic endo-illumination system, which can enable surgeons to operate with two active surgical tools bimanually by providing robotic intraocular illumination.

Some embodiments of the current invention can include some, all, or any combination of the following features.

1. A sensorized ophthalmic endo-illuminator that can sense forces applied along the tool shaft and location where the forces are applied on the tool shaft. For intraocular surgeries, a typical sensorized endo-illuminator is to measure forces at the tip, forces at the sclerotomy site, and the location of the sclerotomy along the tool body, i.e., insertion depth. A current prototype uses fiber optic strain sensors, fiber Bragg gratings. However, any strain sensors can be used to realize the sensing design of this endo-illuminator.
2. When the sensorized endo-illuminator described in (1) is in freehand use, forces at the tool tip and along the tool shaft as well as tool insertion depth and tool movement can be measured. These measurements can be used to assess and assist surgical training, quantify surgical maneuvers during procedures, and provide detailed surgical records.
3. Sensory substitution, e.g., using auditory cues, can be used to provide feedback to users/surgeons based on measurements of tool forces and movements. This sensory substitution feedback can be enabled in freehand use as well as in robotic use.
4. When the sensorized endo-illuminator described in (1) is incorporated into a robot, this robot can hold this endo-illuminator and actively follow the eye movement that is controlled by surgeons. This robotic endo-illumination system can minimize forces exerted between the sclerotomy and the endo-illuminator shaft. The robot control can constrain the motion of this endo-illuminator so that this endo-illuminator moves along with the sclerotomy when the eye moves. Additionally possible movements of this endo-illuminator include pivoting about the sclerotomy and translation along the tool axis of this endo-illuminator. Surgeons then can use both hands to use active surgical tools to perform bimanual procedures.
5. The robotic endo-illumination system described in (4) can maintain a safe insertion depth, avoiding potentially dangerous large insertion depth.
6. The intraocular illumination level, e.g., light intensity, can be measured with other devices, e.g., real-time microscopic image/video. This intraocular illumination level can then be used as a feedback signal. The robotic endo-illumination system described in (4) can servo the intraocular illumination level to the desired value.
7. Tool tracking can be realized by applying computer vision techniques to the real-time microscopic video. Combining tracking of the active surgical tools with the robotic endo-illumination system described in (4), the robotic endo-illuminator can (a) actively avoid collision with other tools, and (b) actively aim toward the region of interest where the active surgical tools are operating.

8. The region of interest is also the region of the patient's retina where the surgeon is viewing through a surgical microscope. An initial registration between the robotic endo-illumination system and the microscope coordinate system can be obtained. The robotic endo-illumination system described in (4) can then actively control the orientation of the endo-illuminator so that the center axis of the illumination intersects with the microscope optical axis at the region of interest.

9. The robotic endo-illumination system described in (4) can also work with other robotic tools. The features 5-8 described above can also be realized with multiple robotic tools collaborating with this robotic endo-illumination system.

Figure 2:
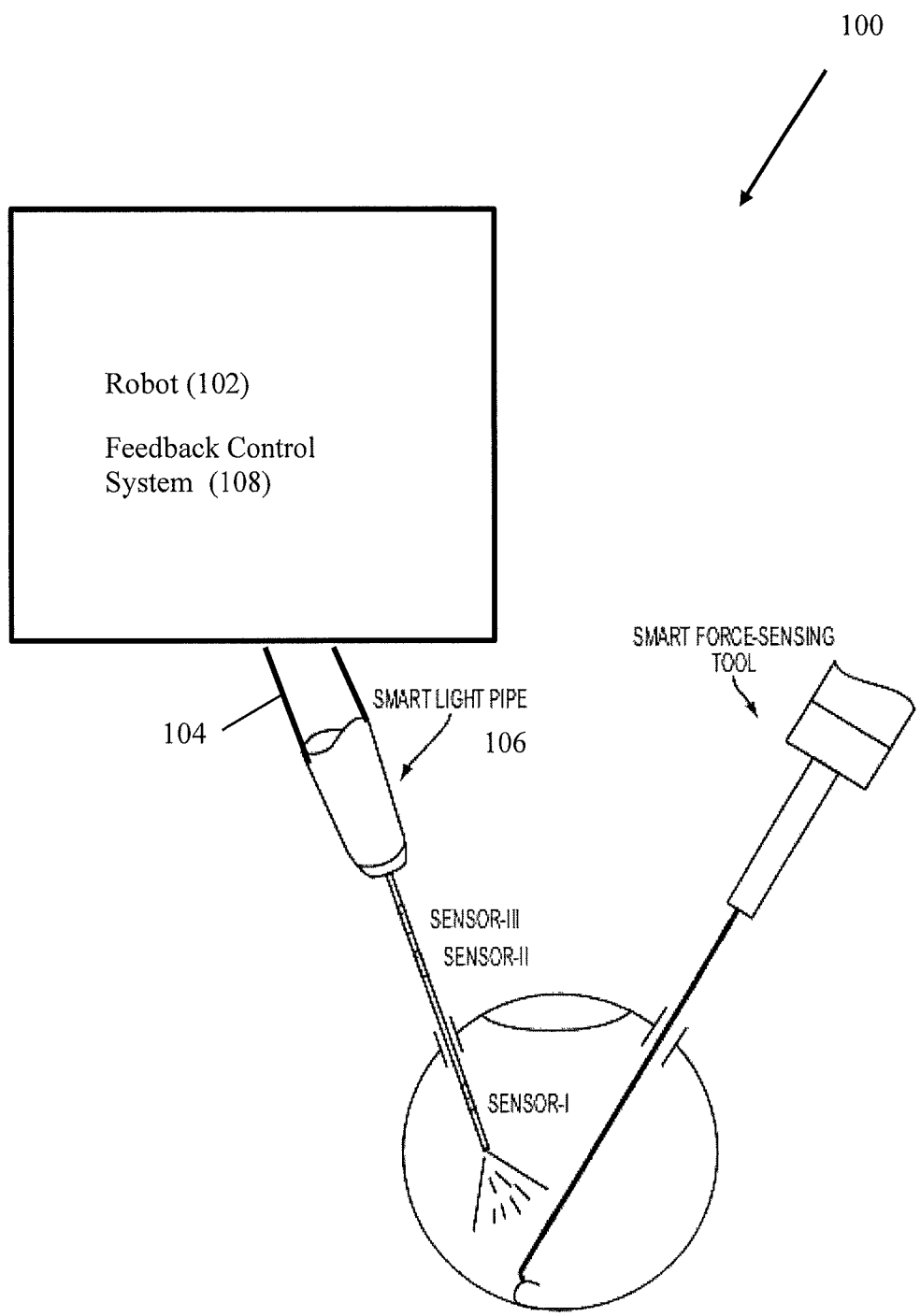
FIG. 2 is a schematic illustration of a surgical system that provides hands-free control of at least one surgical tool according to an embodiment of the current invention.

FIG. 2 is a schematic illustration of a surgical system 100 providing hands-free control of at least one surgical tool according to an embodiment of the current invention. The surgical system 100 includes a robot 102 having a tool connector 104, a smart tool 106 attached to the tool connector 104 of the robot 102, and a feedback control system 108 configured to communicate with the smart tool 106 to provide feedback control of the robot 102. The robot 102 can be, but is not limited to, a fully automated robot in some embodiments. For example, the robot 102 can be a fully automated RCM robot. The surgeon then can have two hands free, one of which can be used to operate a tool, such as, but not limited to the smart force-sensing tool shown in FIG. 2. The smart force-sensing tool shown in FIG. 2 could be operated completely manually and/or while connected to a cooperative control robot. The cooperative control robot can also be an RCM robot, except it provides cooperative control rather than fully automated control. The surgeon could also use a second tool for two-hand operation, for example. In that case, the second tool could also be operated either manually, or while attached to a cooperative control RCM robot, for example. The smart tool 106 can be, but is not limited to, a light pipe. However, a light pipe that is operated in a fully automated mode can be very useful to allow the surgeon to perform two-hand manipulations without encountering lighting problems.

Figure 3:
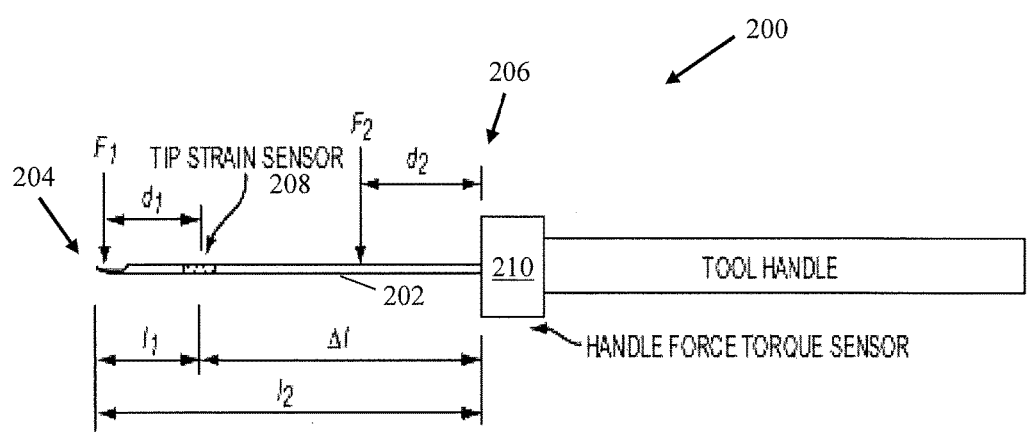
FIG. 3 is a schematic illustration of a smart surgical tool according to an embodiment of the current invention.

FIG. 3 is a schematic illustration of smart tool 200. Smart tool 106 can use the embodiment of the smart tool 200, but is not limited to only that embodiment. Although the smart tool 200 is illustrated as a surgical pick in FIG. 3, it can also be a light pipe or other surgical tool. In the embodiment of FIG. 3, the smart tool 200 has a tool shaft 202 that has a distal end 204 and a proximal end 206. The smart tool 200 also has a strain sensor 208 arranged at a first position along the tool shaft 202, and at least one of a second strain sensor or a torque-force sensor 210 arranged at a second position along the tool shaft 202. The second position is more towards the proximal end 206 of the tool shaft 202 than the first position. The smart tool 200 also has a signal processor (not shown in FIG. 3) configured to communicate with the strain sensor 208 and the at least one of the second strain sensor or the torque-force sensor 210 to receive detection signals therefrom. The signal processor is a structural component that could be packaged together with the robot 102 and/or the feedback control system 108 in some embodiments. The signal processor could be a programmed device and/or a hard-wired device, such as, but not limited to an ASIC and/or a FPGA, for example.

The signal processor is configured to process the detection signals to determine a magnitude and position of a lateral component of a force applied to the tool shaft 202 when the position of the applied force is between the first and second positions. The lateral component of the force is a component of the force that lies in a plane that is orthogonal to the tool shaft 202 at the position at which the force is applied. The feedback control system 108 controls the robot 102 to move in response to at least the magnitude and position of the lateral component of the force applied to the tool shaft 202 when the position of the applied force is between the first and second positions so as to cancel the force applied to the tool shaft to thereby provide hands-free control of the at least one surgical tool.

In the case in which the smart tool 106, 200 is smart light pipe it can also have at least one of light intensity, duration or spectrum control according to some embodiments.

In some embodiments, the feedback control system can be configured to maintain the smart tool 106, 200 at a fixed position and orientation relative to an eye undergoing a surgical procedure as the eye moves.

In some embodiments, the feedback control system can be configured to maintain the smart light pipe such that a center of illumination from the light pipe substantially coincides with an optical axis of a surgical microscope imaging an eye undergoing a surgical procedure as the eye moves.

In some embodiments, the feedback control system can be configured to override the at least one of the fixed position or orientation relative to the eye upon receiving input information concerning a position and orientation of another tool in order to avoid collision of the smart tool with the other tool.

Another embodiment of the current invention is directed to a method of at least one of providing feedback during a surgical procedure or during a surgical training session. The method includes providing a smart tool, such as in any one of the embodiments of smart tools according to the current invention; using the smart tool during the surgical procedure or the surgical training session; receiving signals from the smart tool regarding at least the magnitude and position of the lateral component of the force applied to the tool shaft during the surgical procedure or the surgical training session; and providing at least one of contemporary feedback during the surgical procedure or the surgical training session based on the received signals.

The following examples describe some embodiments in more detail. The broad concepts of the current invention are not intended to be limited to the particular examples. Further, concepts from each example are not limited to that example, but may be combined with other embodiments of the system.

EXAMPLES

Figures 4A, 4B:
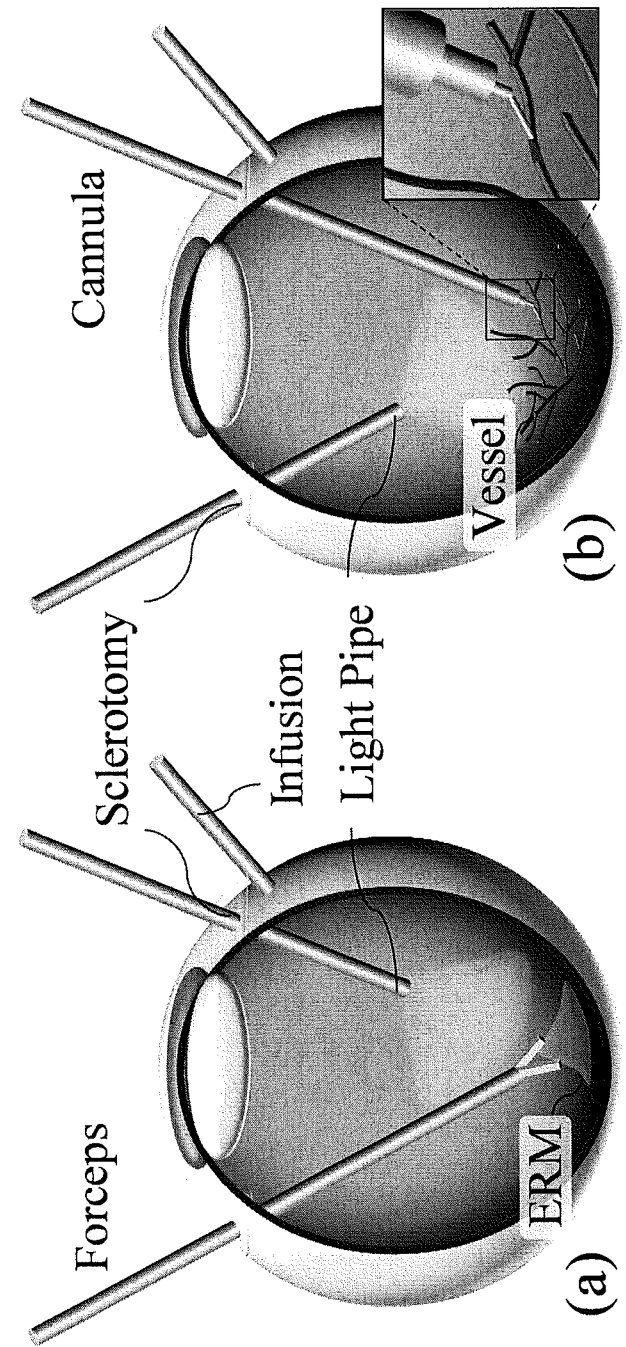
FIGS. 4A-4B show surgical tasks in vitreoretinal surgery; epiretinal membrane (ERM) peeling (a) and retinal vessel cannulation (b).

In vitreoretinal surgery, the surgeon makes multiple self-sealing incisions through the sclera to insert active microsurgical tools (currently as small as 27 Ga) and a light source. For ease of repeated tool access trocars are placed at each site. In order to operate inside of the eye, a retina surgeon typically manipulates an active tool with one hand and directs an illumination source into the surgical field with the other. This permits visualization via a surgical microscope. Vitreoretinal surgery is used to treat blinding eye diseases including but not limited to diabetic retinopathy, macular hole, retinal detachment, and epiretinal membrane (ERM). ERM peeling is a prototypical procedure during which the vitreous body is removed and a pathological, thin semi-transparent membrane is peeled carefully from the retinal surface, as shown in FIG. 4A. An investigational procedure, that has yet to emerge into routine practice, is cannulation of retinal vessels for the delivery of potentially therapeutic agents. In the case of a retinal vein occlusion (RVO), this might include e.g. a thrombolytic agent, see FIG. 4B. During such technically challenging procedures there is a possibility of retina damage. Surgeon hand tremor and inability of the surgeon to feel the forces exerted by the instrument tip to the retina remain significant challenges [1].

In order to overcome the human limitations inherent in freehand retinal microsurgery, many surgical robot systems have been developed. One major category is master-slave teleoperated robots which can achieve precise tool positioning with motion scaling [2]. Other research groups also have proposed handheld robotic devices [3], and wireless microrobots using electromagnets [4]. Our group uses the hands-on cooperative control with the Steady-Hand Eye Robot [5]-[7]. The Eye Robot has five degrees-of-freedom (DOF) which are three translations (x, y, and z) and two rotations (about x and y). A tool is attached to the robot end effector with a quick release mechanism. The user and the robot both hold the tool. The robot follows the user motion with admittance velocity control. The human hand tremor can be damped by the robot's material stiffness. We measure the forces at the tip of the instrument and also on the sclera at the point of insertion, as well as along the intraocular segment of the instrument by using three fiber Bragg grating (FBG) sensors embedded in the instrument. Using the sclera force and its location, the robot can provide force scaling haptic feedback and motion constraint through virtual fixture [8].

Adequate intraocular illumination is critical for visualization of the patient's retinal pathology with the surgical microscope. However, the spectrum of light used includes blue light that is potentially toxic with extended use. Surgeons need to remain cognizant of accumulating light toxicity. Light toxicity is thought to increase significantly after on the order of 13 minutes and avoidance of light toxicity in the macula is essential for good visual outcomes [9]. During light pipe use, a force is applied to the sclera by the light pipe at its point of contact. This force varies as the surgeon repositions the eyeball to accommodate changing surgical views. In vitreoretinal surgery, the surgeon needs to control the surgical tool with one hand, and the light pipe with the other. Bimanual techniques with two surgical instruments have the potential to provide precise and rapid tissue manipulation, with capabilities exceeding uni-manual procedures. In current practice, to achieve bimanual freedom, a surgeon may use either a chandelier light or an illuminated surgical tool. The chandelier light can provide adequate diffuse illumination inside the eye, and does not require a human hand to operate. However, the standard light pipe still provides superior illumination for microsurgery. The illuminated surgical tool can be substituted as a standard light pipe. However when the tool is required, the somewhat dim light source is brought in close proximity to the tissue and has limited flexibility in providing for variable visualization needs. K. Cao et al. have developed an endo-illuminator using shape-memory alloys [10]. Their illuminator tracks the instrument's tip automatically with a bending tip inside the eye. However, it assumes the eye is kept still, and cannot track the eyeball motion during surgery.

In this example, we describe a FBG-sensorized smart light pipe to provide robotic intraocular illumination according to an embodiment of the current invention. The light pipe can measure the scleral contact force on the shaft. The Steady-Hand Eye Robot is used as a "third hand" to hold the light pipe, and to follow the motion of the patient's eyeball.

In this example we demonstrate this system's potential to enable easy bimanual procedures while maintaining excellent illumination without increasing the risk for light toxicity.

Sensorized Light Pipe

Concept

Figures 5A, 5B, 5C, 5D, 5E, 5F:
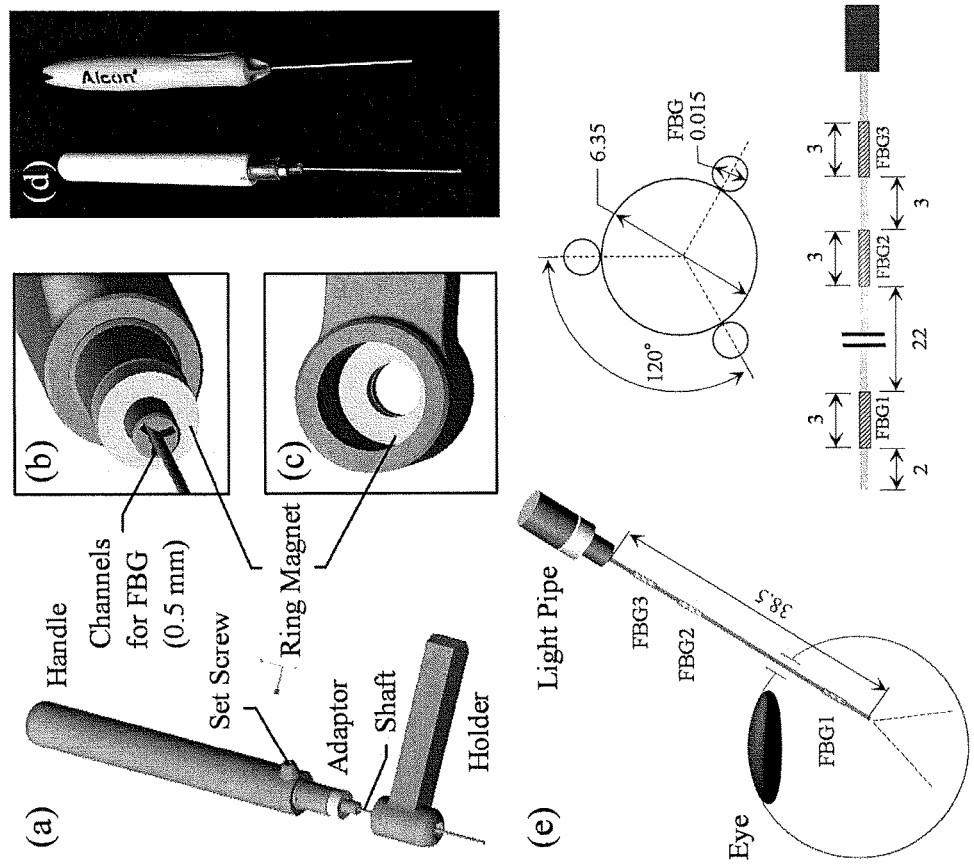
FIGS. 5A-5F show an example of a smart light pipe and quickly detachable holder (a) according to an embodiment of the current invention. Two neodymium ring magnets (ID: ⅛ inch, OD: ¼ inch) are attached to the tip of the middle part (b) and inside of the holder (c). The smart light pipe (left) uses a commercial light pipe (right) (d). Dimensions of the smart light pipe and FBG placement and configuration (e).

The smart light pipe has a shaft, an adaptor, and a handle as illustrated in FIG. 5A. The smart light pipe can be used for both freehand and robot-assisted operations. The dimension of the handle (length: 70 mm, outside diameter: 10 mm) is similar to the commercial light pipe. The light pipe can be easily attached to and detached from the robot tool holder via a magnet-based quick-release mechanism. Two ring magnets (maximum pull force: 5.8 N) are placed on the smart light pipe adaptor and in the robot tool holder, respectively, as illustrated in FIGS. 5B and 5C. This mechanism engages the light pipe with the robot for normal manipulation, and enables emergency tool retraction for safety. As shown in FIG. 5D, we disassembled a commercial light pipe (Alcon, 23 Ga), and separated the optical fiber to attach to our light pipe adaptor. It was then fixed to the handle using a set screw.

In order to measure the scleral force on the light pipe, we integrated three optical fibers onto the light pipe shaft. Each fiber has three FBG sensors (Technica S.A., Beijing, China), as shown in FIG. 5E. All three FBG sensors in each fiber are 3 mm long. The center wavelengths of the FBGs are 1526.8 nm, 1531.3 nm, and 1534.8 nm from the distal FBG sensor to the proximal one. Three optical fibers are manually aligned and fixed on the light pipe shaft with 120° interval. The transverse forces applied to the light pipe shaft are measured by detecting the wavelength shifts of the FBG sensors with the sm130-700 optical sensing interrogator (Micron Optics, Atlanta, Ga.) which has a 2 kHz fresh rate and 1525-1565 nm spectrum range. The FBG sensor at the tip (FBG1) is used for detecting collisions of the eye tissue with the other instrument. The sclera FBG sensors (FBG2 and FBG3) placed outside of the eye are used to measure the contact forces between the light pipe and the location of the sclerotomy with respect to the light pipe.

Calibration

We conducted an extensive calibration of the smart light pipe using an automated calibration system. Here the smart light pipe is controlled by a high precision robot (translation: 1 μm, rotation: 0.005°). The force ground truth is measured by a precision scale (Sartorius AG, Goettingen, Germany) with a resolution of 1 mg. These calibrations follow the same procedures used in prior work [8].

Figures 6A, 6B, 6C, 6D:
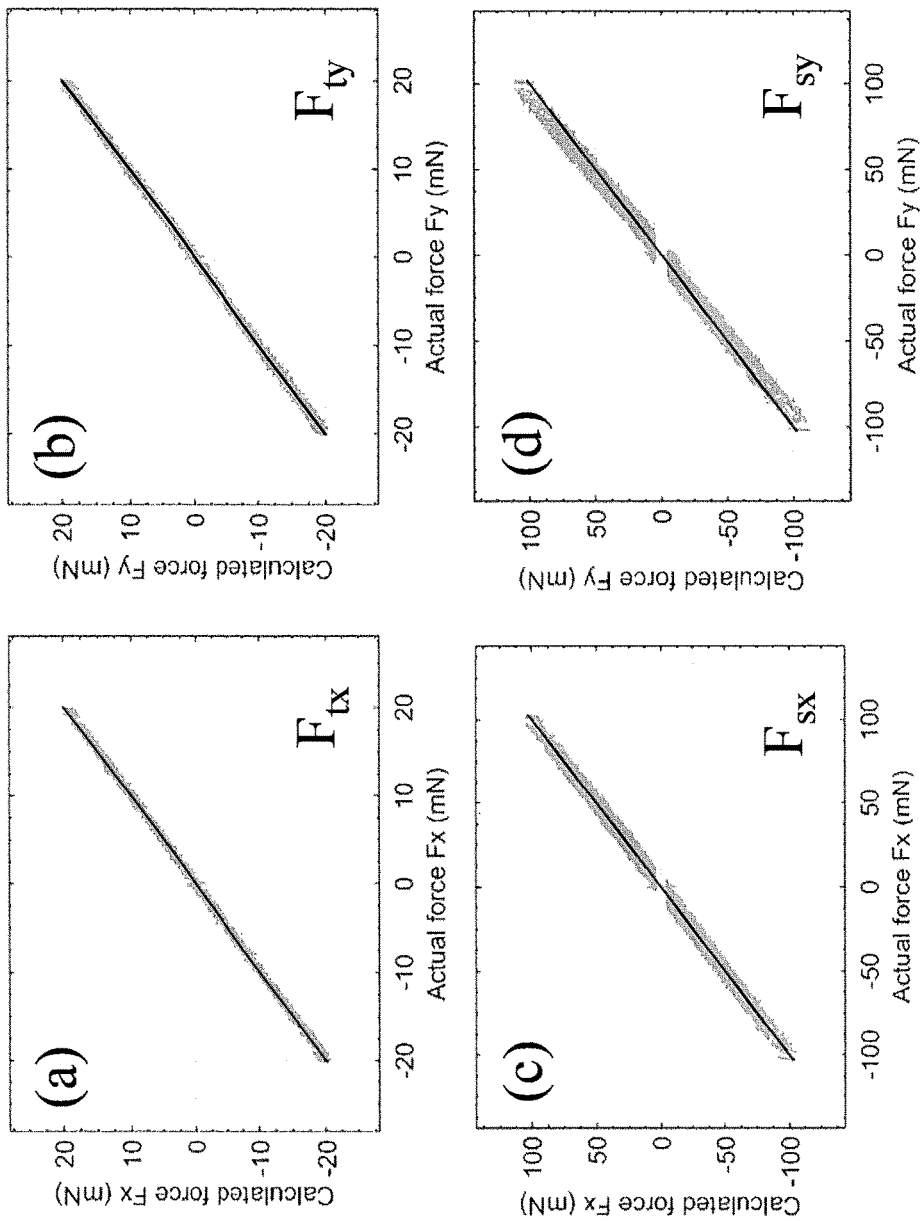
FIGS. 6A-6D show calibration results. The calculated tip forces versus the actual tip forces in X and Y directions (a)(b). The calculated scleral forces versus the actual forces on sclera in X and Y directions (c)(d).
Figures 7A, 7B, 7C, 7D:
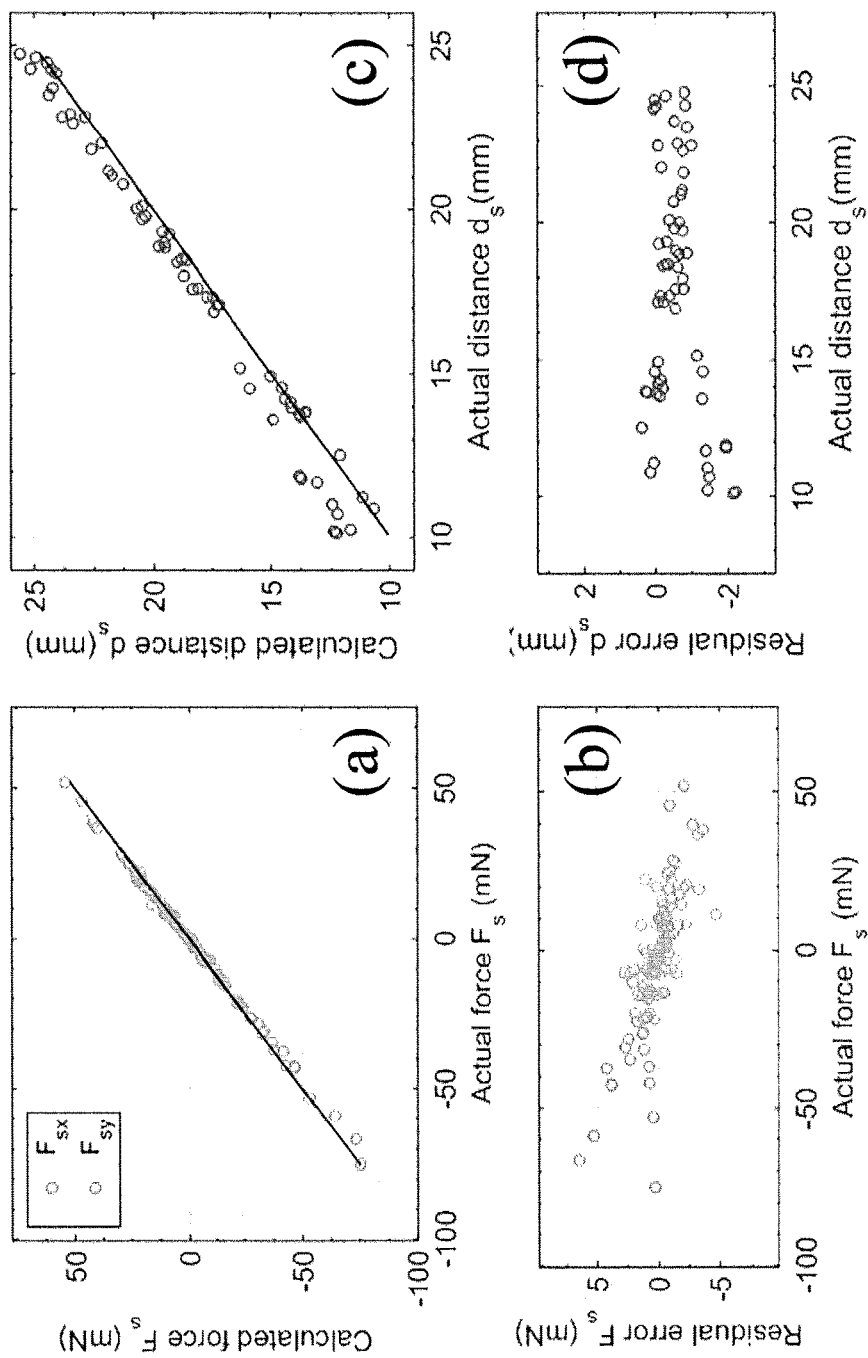
FIGS. 7A-7D show results of validation of FBG sensor calibration. The calculated sclera forces using calibration information against the actual scleral forces (a) and its residual error from the actual force (b). The calculated location of the sclerotomy against the actual sclerotomy location (c) and its residual error from the actual distance (d).

FIGS. 6A and 6B illustrate the calculated tip forces versus the actual tip forces in X and Y directions; FIGS. 6C and 6D show the calculated sclera forces versus the actual sclera forces in X and Y directions. The straight lines show the ideal match with slope 1. The root mean square (RMS) of the residual errors are 0.31 mN and 0.36 mN for the tip X- and Y-forces, 0.98 mN and 1.24 mN for the sclera X- and Y-forces, respectively. As for the sclerotomy location with respect to the tip of the light pipe, it is estimated using forces larger than 5 mN in magnitude, and the average RMS error is 1.7 mm.

In order to validate the calibration results, we carried out validation experiments using the automated calibration system. The location, direction and magnitude of the applied force are generated randomly within the calibrated range. FIGS. 7A-7D illustrate the experimental results. The RMS error of the calculated sclera force versus the actual sclera force is 0.79 mN for $F_{sx}$ and 2.14 mN for $F_{sy}$. The RMS error of the estimated location of the sclerotomy is 0.83 mm.

EXPERIMENTS AND RESULTS

Here we conduct experiments to evaluate the automated intraocular illumination provided by the smart light pipe and the robot. Variable admittance control proposed in [8] is used to enable the robotic light pipe to comply with the eye movement.

Figures 8A, 8B, 8C, 8D:
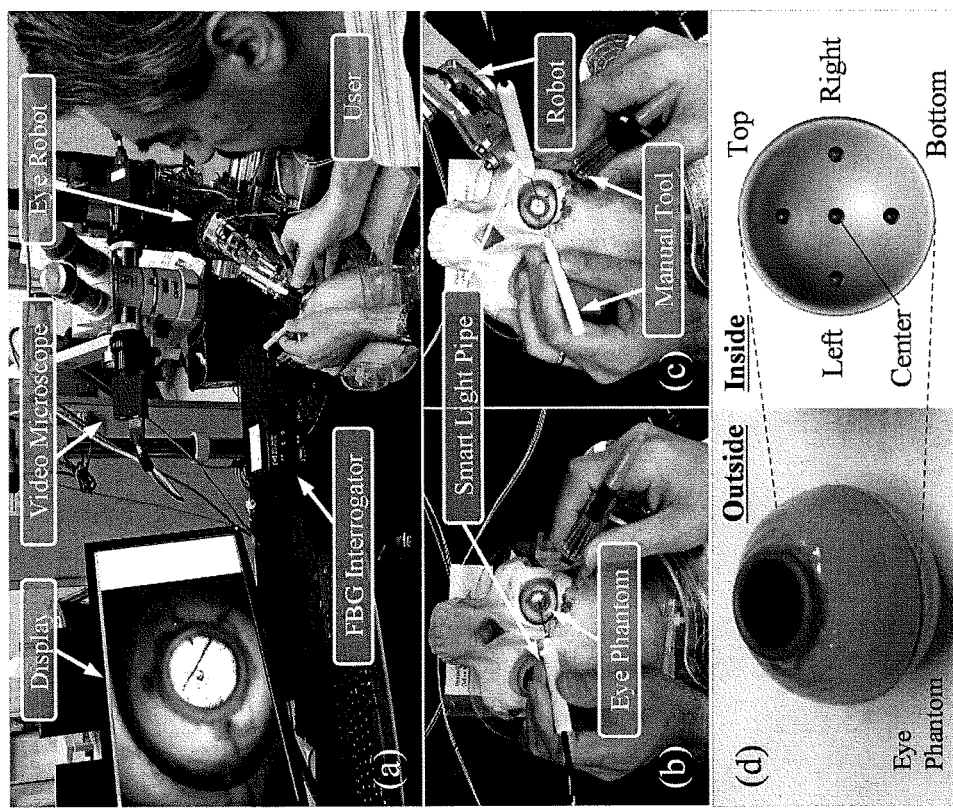
FIGS. 8A-8D show an experimental setup. A user manipulates tools held on both hands while watching the view from the microscope (a). We prepare two operating conditions: freehand operation (b) and robot-assisted operation (c). Five spherical markers are placed inside of the eye phantom (d).

Intraocular visualization is provided by a display showing the microscopic view, as shown in FIG. 8A. Two experimental conditions are used; (I) Freehand: manipulating a manual tool with the dominant hand and a smart light pipe with the non-dominant hand, as shown in FIG. 8B; (II) Robot-assisted: manipulating manual tools with both hands while the smart light pipe is held by the robot and inserted through an additional incision, as shown in FIG. 8C. We made an eye phantom that had five small spherical makers (1.5 mm diameter) placed in a cross shape on the retina, as illustrated in FIG. 8D. Four markers are set around a center marker (top, bottom, left and right). Operationally the subject moves the eye phantom in a standard surgical fashion using the surgical tools such that the desired marker is positioned at the center of the microscopic view. Each trial starts from and ends at the center marker and the other marker order is determined randomly. The subject conducts 10 trials under each operating condition. In operating condition (II), with robot-assisted illumination, the initial position of the light pipe is set by the user, as the preferred illumination inside the eye. In this experiment, we record the microscopic view during the predetermined task. The subject verbally informs the experiment conductor when he or she thinks the target marker is at center of the microscopic view. A snapshot of the microscopic view is then taken. The images are transformed to gray-scale, and the view of the retina is segmented using MATLAB image processing tool box. The light intensity results are compared between the two experimental conditions. We also record the scleral forces applied on the light pipe.

Figures 9A, 9B:
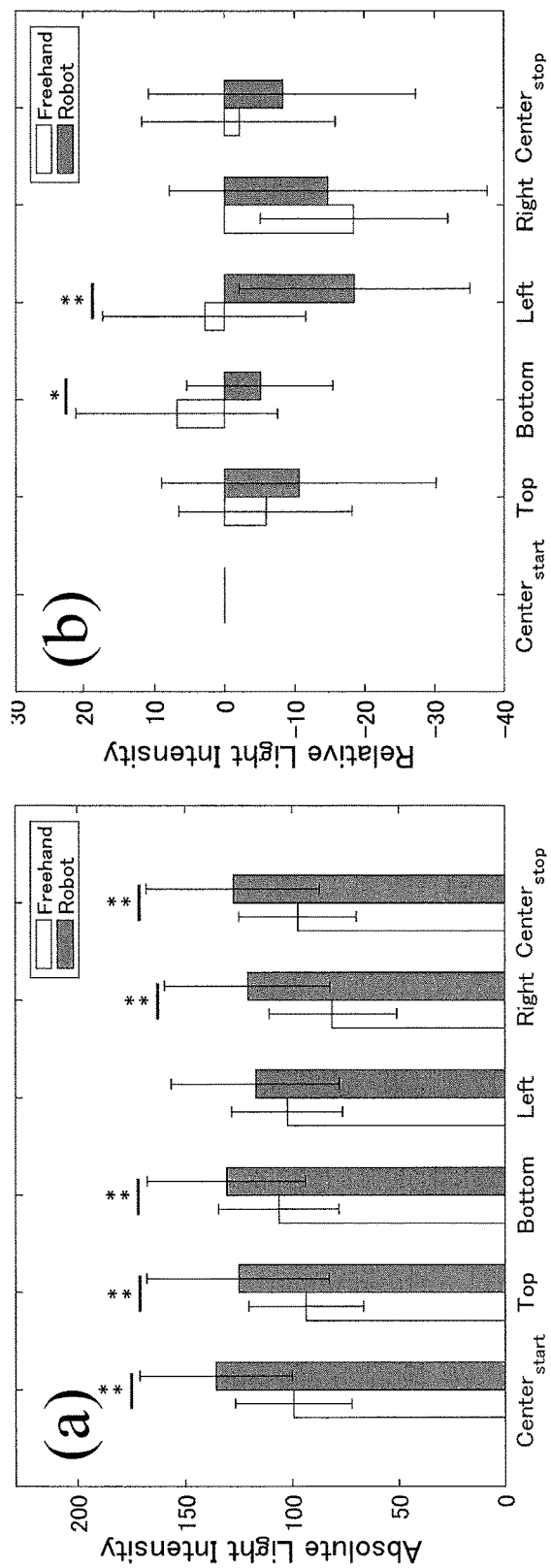
FIGS. 9A-9B show absolute light intensity (a) and the relative light intensity with respect to the starting marker position (b) at each marker for freehand and robot-assisted conditions.
Figures 10A, 10B:
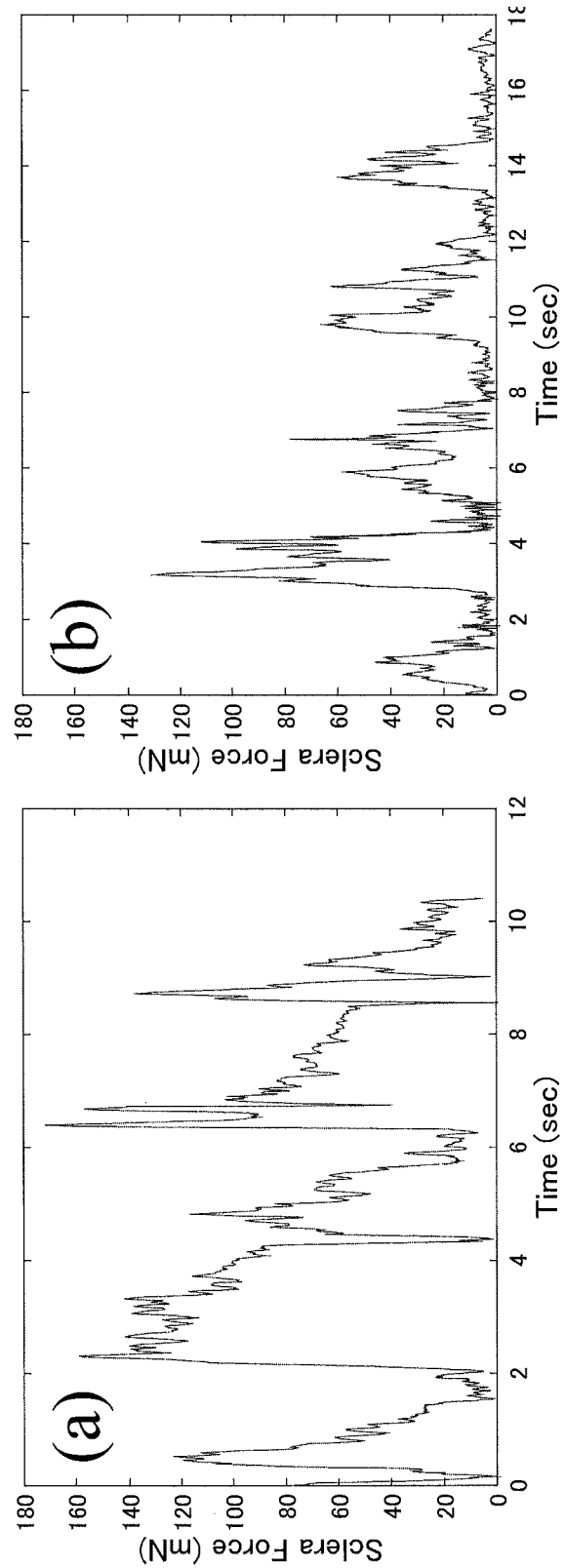
FIGS. 10A-10B show sclera forces applied on the smart light pipe during one trial for freehand condition (a) and robot-assisted condition (b).

Four subjects (one retinal surgeon and three engineers) participated in this experiment. FIGS. 9A-9B show the light intensity recorded at each marker position. The average light intensity is higher in the robot-assisted test, as compared to that in the freehand test, as shown in FIG. 9A. As the subjects tend to set the initial illumination at a higher intensity during the robot-assisted trials, the illumination change at the other marker positions with respect to the start position is shown in FIG. 9B to visualize the relative light intensity at each marker position. FIGS. 10A and 10B show examples of the sclera forces applied on the smart light pipe in two experimental conditions. The marker orders in the cases of the freehand and robot conditions are Center-Bottom-Left-Top-Right-Center and Center-Right-Bottom-Left-Top-Center, respectively. The five peaks in these graphs correspond to each marker position. The average maximum sclera force in the robot-assisted condition for each subject are shown in Table 1. In the freehand experiments, the sclera forces exceed the designed range of the FBG wavelength shifts. The calculated force saturated and became invalid.

DISCUSSION AND CONCLUSION

While in this set of experiments we observed that the average light intensity was higher with use of the robotic light pipe; this was largely due to the initial selection of a higher preferred light intensity by the human user. This initial setting was a condition established by the user prior to start of the experimental tasks in condition II and was not a requirement for the conduct of condition I, manual use. If however, we use the initial light intensity level at the start position of each trial as the reference and index it to the average light intensity at the target we see that the light intensity is increased at some marker positions and decreased at others during freehand use while it is decreased at all marker positions during robot assisted use. There are three marker positions where the freehand and robot-assisted conditions have no significant difference, i.e., the robotic light pipe provides similar illumination as the subject does with manual control. Two marker positions show significant differences, where the subjects increase the average light intensity while the robotic light pipe reduces it. The control method of the robotic light pipe mainly commands the lateral translational DOFs. It does not fully take advantage of the translation along the light pipe axis or rotational DOFs. Currently, the light pipe does not actively track the region of interest or reorient the illumination. In other embodiments we can incorporate additional input information, e.g., the microscopic video, and also utilize all of the available DOFs.

The force exerted between the light pipe and the sclera was measured during both experimental conditions. However, the scleral forces in the two experimental methods are not directly comparable. In the robot-assisted condition, the smart light pipe follows the eye movement to minimize the force exerted at the sclerotomy. It does not actively exert force to move the eye. However, in the freehand condition, the smart light pipe is used to actively move the eye. Therefore, the exerted scleral forces are intentional, thus are much larger. As shown in FIGS. 10A-10B, the scleral force during freehand manipulation is larger than that in the robot-assisted condition. This selected freehand trial was one of the few trials with non-saturated scleral forces. The overall average maximum scleral force was acceptable as the maximum scleral forces were above 150 mN in our previous in-vivo experiments.

These results show that a robot-controlled light pipe can provide adequate intraocular illumination without introducing significant additional force load on the sclera. These methods, techniques and tools are first steps towards improving bimanual procedures for retinal microsurgery. Optimization of target illumination while minimizing light toxicity in the macula as well as minimization of applied scleral forces can be included.

REFERENCES

[1] P. Gupta, P. S. Jensen, and E. de Juan, "Surgical forces and tactile perception during retinal microsurgery," in

TABLE 1

Mean of the maximum scleral forces in the robot-assisted operating condition for four subjects.

| Subject | A | B | C | D | Overall |
|---|---|---|---|---|---|
| Force (mN) | 126.00 ± 23.99 | 95.78 ± 24.71 | 79.94 ± 26.24 | 126.53 ± 38.70 | 107.06 ± 28.41 |

International Conference on Medical Image Computing and Computer-Assisted Intervention, vol. 1679, 1999, pp. 1218-1225.
[2] D. H. Bourla, J. P. Hubschman, M. Culjat, A. Tsirbas, A. Gupta, and S. D. Schwartz, "Feasibility study of intraocular robotic surgery with the da Vinci surgical system," Retina Philadelphia Pa, vol. 28, no. 1, pp. 154-158, January 2008.
[3] C. Song, D. Y. Park, P. L. Gehlbach, S. J. Park, and J. U. Kang, "Fiber-optic OCT sensor guided "SMART" microforceps for microsurgery," Biomedical Optics Express, vol. 4, no. 7, pp. 1045-1050, 2013.
[4] M. P. Kummer, S. S. Member, J. J. Abbott, B. E. Kratochvil, R. Borer, A. Sengul, and B. J. Nelson, "OctoMag: An Electromagnetic System for 5-DOF Wireless Micromanipulation," IEEE Transactions on Robotics, vol. 26, no. 6, pp. 1006-1017, 2010.
[5] R. Taylor, P. Jensen, L. Whitcomb, A. Barnes, R. Kumar, D. Stoianovici, P. Gupta, Z. Wang, E. Dejuan, and L. Kavoussi, "A Steady-Hand Robotic System for Microsurgical Augmentation," The International Journal of Robotics Research, vol. 18, no. 12, pp. 1201-1210, 1999.
[6] B. Mitchell, J. Koo, I. Iordachita, P. Kazanzides, A. Kapoor, J. Handa, G. Hager, and R. Taylor, "Development and application of a new steady-hand manipulator for retinal surgery," in IEEE International Conference on Robotics and Automation, 2007, pp. 623-629.
[7] A. Uneri, M. A. Balicki, J. Handa, P. Gehlbach, R. H. Taylor, and I. Iordachita, "New Steady-Hand Eye Robot with micro-force sensing for vitreoretinal surgery," in IEEE International Conference on Biomedical Robotics and Biomechatronics, 2010, pp. 814-819.
[8] X. He, M. Balicki, P. Gehlbach, J. Hanada, R. Taylor, and I. Iordachita, "A multi-function force sensing instrument for variable admittance robot control in retinal microsurgery," in IEEE International Conference on Robotics and Automation, 2014, pp. 1411-1418.
[9] Tomas H. W, Vitreoretinal Surgery. Springer Berlin Heidelberg, 2013, ch. 2.
[10] K. Cao, R. Pinon, I. Schachar, T. Jayasundera, and S. Awtar, "Automated Instrument Tracking Endo-Illuminator for Intra-Ocular Surgeries," Journal of medical Devices, vol. 8, no. 3, pp. 030932, 2014.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A surgical system providing hands-free control of at least one surgical tool, comprising:
 a robot having a tool connector;
 a smart tool attached to said tool connector of said robot; and
 a feedback control system configured to communicate with said smart tool to provide feedback control of said robot,
 wherein said smart tool comprises:
 a tool comprising a tool shaft having a distal end and a proximal end;
 a strain sensor arranged at a first position along said tool shaft;
 at least one of a second strain sensor or a torque-force sensor arranged at a second position along said tool shaft, said second position being more towards said proximal end of said tool shaft than said first position; and
 a signal processor configured to communicate with said strain sensor and said at least one of said second strain sensor or said torque-force sensor to receive detection signals therefrom,
 wherein said signal processor is configured to process said detection signals to determine a magnitude and position of a lateral component of a force applied to said tool shaft when said position of said applied force is between said first and second positions,
 wherein said lateral component of said force is a component of said force that lies in a plane that is orthogonal to said tool shaft at said position at which said force is applied, and
 wherein said feedback system controls said robot to move in response to at least said magnitude and position of said lateral component of said force applied to said tool shaft when said position of said applied force is between said first and second positions so as to cancel said force applied to said tool shaft to thereby provide hands-free control of said at least one surgical tool.

2. The surgical system according to claim 1, wherein said smart tool is a smart light pipe.

3. The surgical system according to claim 2, wherein said smart light pipe has at least one of light intensity, duration or spectrum control.

4. The surgical system according to claim 2, wherein said robot is a retinal microsurgery robot.

5. The surgical system according to claim 4, wherein said feedback system is configured to maintain said smart light pipe at a fixed position and orientation relative to an eye undergoing a surgical procedure as said eye moves.

6. The surgical system according to claim 5, wherein said smart light pipe has at least one of light intensity, duration or spectrum control.

7. The surgical system according to claim 6, wherein said feedback system is further configured to override said at least one of said fixed position or orientation relative to said eye upon receiving input information concerning a position and orientation of another tool in order to avoid collision of said smart light pipe with said another tool.

8. The surgical system according to claim 5, wherein said feedback system is further configured to override said at least one of said fixed position or orientation relative to said eye upon receiving input information concerning a position and orientation of another tool in order to avoid collision of said smart light pipe with said another tool.

9. The surgical system according to claim 4, wherein said feedback system is configured to maintain said smart light pipe such that a center of illumination from said light pipe substantially coincides with an optical axis of a surgical microscope imaging an eye undergoing a surgical procedure as said eye moves.

10. The surgical system according to claim 9, wherein said smart light pipe has at least one of light intensity, duration or spectrum control.

11. The surgical system according to claim 10, wherein said feedback system is further configured to override said at least one of said fixed position or orientation relative to said eye upon receiving input information concerning a position and orientation of another tool in order to avoid collision of said smart light pipe with said another tool.

12. The surgical system according to claim 9, wherein said feedback system is further configured to override said at least one of said fixed position or orientation relative to said eye upon receiving input information concerning a position and orientation of another tool in order to avoid collision of said smart light pipe with said another tool.

13. The surgical system according to claim 1, wherein said robot is a retinal microsurgery robot.

14. The surgical system according to claim 13, wherein said feedback system is configured to maintain said smart tool at a fixed position and orientation relative to an eye undergoing a surgical procedure as said eye moves.

15. The surgical system according to claim 14, wherein said feedback system is further configured to override said at least one of said fixed position or orientation relative to said eye upon receiving input information concerning a position and orientation of another tool in order to avoid collision of said smart tool with said another tool.

16. The surgical system according to claim 14, wherein said smart tool is a smart light pipe that has at least one of light intensity, duration or spectrum control.

17. A method of at least one of providing feedback during a surgical procedure or during a surgical training session, comprising:
  providing a smart tool comprising:
    a tool comprising a tool shaft having a distal end and a proximal end,
    a strain sensor arranged at a first position along said tool shaft,
    at least one of a second strain sensor or a torque-force sensor arranged at a second position along said tool shaft, said second position being more towards said proximal end of said tool shaft than said first position, and
    a signal processor configured to communicate with said strain sensor and said at least one of said second strain sensor or said torque-force sensor to receive detection signals therefrom,
  wherein said signal processor is configured to process said signals to determine a magnitude and position of a lateral component of a force applied to said tool shaft when said position of said applied force is between said first and second positions,
  wherein said lateral component of said force is a component of said force that lies in a plane that is orthogonal to said tool shaft at said position at which said force is applied, using said smart tool during said surgical procedure or said surgical training session;
  receiving signals from said smart tool regarding at least said magnitude and position of said lateral component of said force applied to said tool shaft during said surgical procedure or said surgical training session; and
  providing at least one of contemporary feedback during said surgical procedure said surgical training session based on said received signals.

18. The method of claim 17, wherein said smart tool is a smart light pipe.

19. A smart surgical tool, comprising:
  a tool handle configured to be hand-held and to be attachable to and detachable from a robotic system, said tool handle having a proximal end and a distal end;
  a tool shaft attached to a distal end of said tool handle, said tool shaft having a distal end and a proximal end;
  a first strain sensor arranged at a first position along said tool shaft; and
  at least one of a second strain sensor or a torque-force sensor arranged at a second position along said tool shaft, said second position being more towards said proximal end of said tool shaft than said first position,
  wherein said tool handle has a quick-release portion to allow a user to remove said smart surgical tool from said robotic system to avoid or minimize damage during surgery if said robot malfunctions,
  wherein the first strain sensor, the at least one of the second strain sensor, or both is configured to output detection signals to a signal processor, said detection signals being processed by the signal processor to output a control signal to a feedback control system to control said robotic system to move in response to said control signal, the control signal corresponding to a magnitude and position of a lateral component of a force applied to said tool shaft, said lateral component of said force is a component of said force that lies in a plane that is substantially orthogonal to said tool shaft at a position at which said force is applied.

20. The smart surgical tool according to claim 19, wherein said smart surgical tool is a smart surgical light pipe.

* * * * *